US012589023B2

(12) United States Patent
Nielsen

(10) Patent No.: US 12,589,023 B2
(45) Date of Patent: **\*Mar. 31, 2026**

(54) CONVEX OSTOMY BARRIER AND METHOD OF FORMING CONVEX OSTOMY BARRIERS OF VARIOUS SOFTNESS

(71) Applicant: HOLLISTER INCORPORATED, Libertyville, IL (US)

(72) Inventor: Kenneth Nielsen, Ålsgårde (DK)

(73) Assignee: HOLLISTER INCORPORATED, Libertyville, IL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/758,303

(22) Filed: Jun. 28, 2024

(65) Prior Publication Data

US 2024/0350296 A1 Oct. 24, 2024

Related U.S. Application Data

(63) Continuation of application No. 17/263,039, filed as application No. PCT/US2019/050607 on Sep. 11, 2019, now Pat. No. 12,048,642.

(60) Provisional application No. 62/730,109, filed on Sep. 12, 2018.

(51) Int. Cl.
*A61F 5/448* (2006.01)

(52) U.S. Cl.
CPC ...... *A61F 5/448* (2013.01); *A61F 2005/4483* (2013.01)

(58) Field of Classification Search
CPC .. A61F 5/448; A61F 2005/4483; A61F 5/445; A61F 2005/4486; A61F 5/449
See application file for complete search history.

(56) References Cited

U.S. PATENT DOCUMENTS

| | | | |
|---|---|---|---|
| 6,210,384 B1 | 4/2001 | Cline | |
| 6,312,415 B1 | 11/2001 | Nielsen | |
| 2001/0004687 A1* | 6/2001 | Plass ...................... | A61F 5/448 |
| | | | 604/338 |
| 2010/0174256 A1* | 7/2010 | Rosengren .............. | A61F 5/445 |
| | | | 604/344 |

(Continued)

FOREIGN PATENT DOCUMENTS

| | | | | |
|---|---|---|---|---|
| EP | 0415282 A1 | 3/1991 | | |
| FR | 2548014 A2 * | 1/1985 | ............. | A61F 5/445 |
| IE | 46615 B1 * | 8/1983 | ............. | A61F 5/448 |

(Continued)

OTHER PUBLICATIONS

European Search Report issued in connection with EP application No. 25158076.7 dated May 12, 2025, 07 pages.

*Primary Examiner* — Rebecca E Eisenberg
*Assistant Examiner* — Matthew Wrubleski
(74) *Attorney, Agent, or Firm* — Klintworth & Rozenblat LLP

(57) ABSTRACT

A convex ostomy barrier for attaching an ostomy appliance to a peristomal skin surrounding a stoma includes a skin barrier formed from a skin friendly adhesive, an inlet opening for receiving a stoma, and a convex insert system arranged adjacent the skin barrier to provide a convex body-side contour of the convex ostomy barrier. The convex insert system includes a convex insert and a ring, which are configured to be assembled together to form the convex insert system.

6 Claims, 4 Drawing Sheets

(56)         References Cited

U.S. PATENT DOCUMENTS

2020/0253777 A1 *   8/2020  Jones ...................... A61F 5/443

FOREIGN PATENT DOCUMENTS

| WO | WO-9318725 A1 * | 9/1993 | ............. A61F 5/448 |
| WO | WO2018/067539 A1 | 4/2018 | |
| WO | WO2018/093815 A2 | 5/2018 | |

* cited by examiner

SEE FIG. 4B
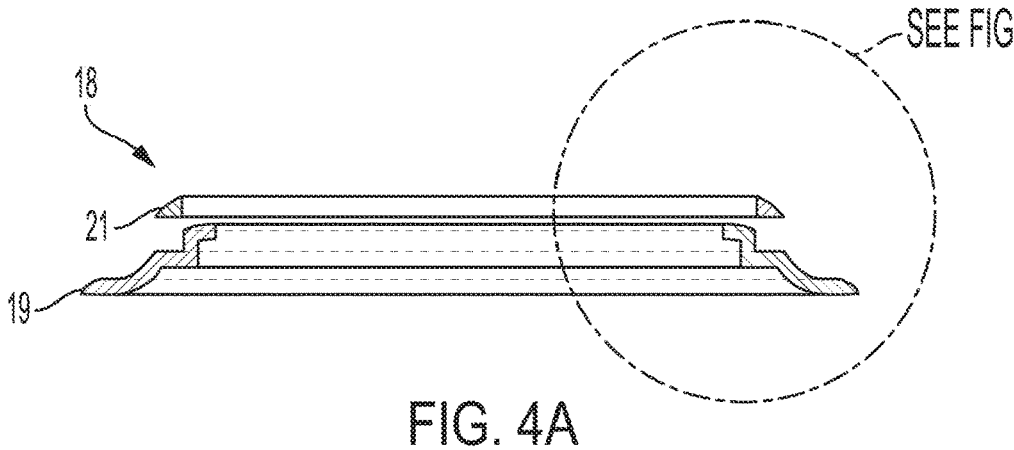
FIG. 4A
FIG. 4B
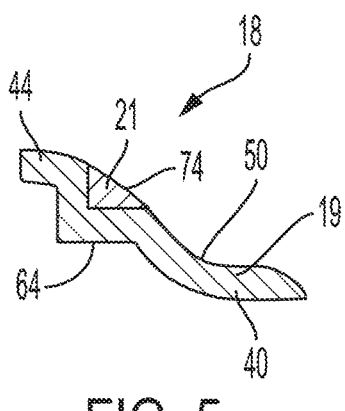
FIG. 5

CONVEX OSTOMY BARRIER AND METHOD OF FORMING CONVEX OSTOMY BARRIERS OF VARIOUS SOFTNESS

This application is a continuation of pending U.S. application Ser. No. 17/263,039 filed dated Jan. 25, 2021 which is a National Stage Application of International Patent Application PCT PCT/US2019/050607 filed dated Sep. 11, 2019 and which claims the benefit of and priority to U.S. Provisional Application No. 63/730,109 filed dated Sep. 12, 2018, the entirety of which are incorporated fully herein by reference.

BACKGROUND

The following description generally relates to ostomy appliances, and in particular, to an ostomy barrier.

Ostomy pouches for collecting bodily waste are used by individuals who have had surgery such as a colostomy, ileostomy, or urostomy. Two common types of ostomy pouch systems are available, to wit, a one-piece pouch system and a two-piece pouch system. In a one-piece pouch system, an ostomy barrier is permanently attached to a pouch. In such a one-piece pouch system, the entire pouch system including the ostomy barrier is removed when a user wants to replace the pouch.

In a two-piece pouch system, a pouch and an ostomy barrier are provided as two separate devices. The two-piece pouch system typically includes a pair of coupling rings, one of which is fixedly attached to the ostomy barrier, while the other is attached to the pouch. The coupling rings are configured to mate with each other, such that the pouch may be securely and removeably attached to the ostomy barrier by engaging the coupling rings together. In use, the ostomy barrier is first attached to a user, and the pouch is secured to the faceplate by engaging the coupling rings together. Thus, two-piece pouch systems allow a user to remove and replace a pouch without removing the ostomy barrier from the user. This can help to reduce the discomfort and irritation associated with removing skin barrier adhesive from user's skin Ostomy barriers are configured to seal against peristomal skin surfaces and protect the peristomal surfaces from exposure to stomal effluent. However, the topography of stomas and peristomal surfaces surrounding stomas varies among patients, and sealing an ostomy appliance against such different peristomal surfaces and stomas remain as an area for further improvements. A person having a stoma that is flush or recessed may find that applying external support or pressure from a barrier in the peristomal region aids in directing the discharge of effluent from the stoma directly into the ostomy pouch. Accordingly, the effectiveness of an adhesive seal between the ostomy barrier and the peristomal skin surface (i.e., a seal formed by the adhesive layer) may be prolonged.

The present disclosure provides an improved flexible convex barrier and a method of making convex barriers of various softness/hardness according to various embodiments.

BRIEF SUMMARY

In one aspect, a convex ostomy barrier for attaching an ostomy appliance to a peristomal skin surrounding a stoma is provided. The convex ostomy barrier may include a skin barrier formed from a skin friendly adhesive, an inlet opening for receiving a stoma, and a convex insert system arranged adjacent the skin barrier and configured to provide a convex body-side contour of the convex ostomy barrier. The convex insert system may include a convex insert and a ring, which may be configured to be assembled together to form the convex insert system.

In an embodiment, the convex insert may include a core-out portion configured to receive the ring. In such an embodiment, the ring may be arranged in the core-out portion of the convex insert to form the convex insert system having a convex ring-like body. The convex insert may include an inner flange, a middle portion including the core-out portion, and an outer flange. The inner flange and the outer flange may be connected by the middle portion and arranged in different axial planes, wherein the convex insert system is configured to support the skin barrier on a body-side surface. In an embodiment, the convex insert may include a radial wall radially extending from the outer flange toward the inlet opening and an axial wall extending axially from the radial wall in a body-side direction, wherein the core-out portion is defined by the radial wall and the axial wall on a body-side. The inner flange may extend from the axial wall toward the inlet opening, and wherein the outer flange, the middle portion, and the inner flange provides a step-like protrusion in the body-side direction.

In some embodiments, the convex ostomy barrier may be configured for a two-piece ostomy pouch system comprising a flange including a coupling ring. The flange may be attached to a pouch-side surface of the radial wall of the convex insert.

The convex ostomy barrier of any of the foregoing embodiments may be configured such that the convex ostomy barrier of various softness/hardness may be provided by using different rings in the convex insert system. For example, the convex ostomy barrier may be configured to have a first softness/hardness by incorporating the convex insert system formed from the convex insert and the ring having a first characteristic, or configured to have a second softness/hardness different than the first softness/hardness by incorporating the convex insert system formed from the convex insert and the ring having a second characteristic.

In another aspect, a method of making convex ostomy barriers of various softness/hardness is provided. The method may include the step of providing a convex insert and a plurality of rings, wherein the convex insert is configured to be assembled with one of the plurality of the rings to form a convex insert system. Each of the rings may be configured to have a different characteristic to provide a different softness/hardness when assembled with the convex insert and used in a convex ostomy barrier. The method may also include the steps of selecting one of the plurality of the rings according to a desired softness/hardness of the convex ostomy barrier, assembling the convex insert and the selected ring together to form the convex insert system, and attaching a skin barrier formed from a skin friendly adhesive to a body-side surface of the convex insert system.

In an embodiment, the plurality of the rings may include a first ring having a first characteristic and a second ring having a second characteristic. The convex insert may be assembled with the first ring to form a first convex insert system for a first convex ostomy barrier, or the convex insert may be assembled with the second ring to form a second convex insert system for a second convex ostomy barrier, wherein the first convex ostomy barrier has a first softness/hardness and the second convex ostomy barrier has a second softness/hardness that is different than the first softness/hardness.

In some embodiments, the step of providing a convex insert and plurality of rings may include the step of providing the convex insert including a core-out portion configured to receive one of the plurality of rings. In such embodiments, the step of assembling the convex insert and the selected ring may comprise arranging the selected ring in the core-out portion of the convex insert to form the convex insert system having a convex ring-like body. The convex insert may include an inner flange, a middle portion including the core-out portion, and an outer flange, wherein the inner flange and the outer flange are connected by the middle portion and arranged in different axial planes. The convex insert system may be configured to support the skin barrier on a body-side surface.

In an embodiment, the convex insert may include a radial wall radially extending from the outer flange toward the inlet opening and an axial wall extending axially from the radial wall in a body-side direction, wherein the core-out portion is defined by the radial wall and the axial wall on a body-side. The inner flange may extend from the axial wall toward the inlet opening, wherein the outer flange, the middle portion, and the inner flange provide a step-like protrusion in the body-side direction.

The method of any of the foregoing embodiments may further include the step of providing a flange including a coupling ring, wherein the flange is attached to a pouch-side surface of the radial wall of the convex insert.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein:

FIGS. 4A and 4B are schematic cross sectional views of the convex insert system of FIG. 3 taken along 4-4;

FIG. 5 is a schematic cross sectional view of the convex insert system of FIGS. 4A and 4B showing the ring received in the convex insert;

DETAILED DESCRIPTION

Figure 1:
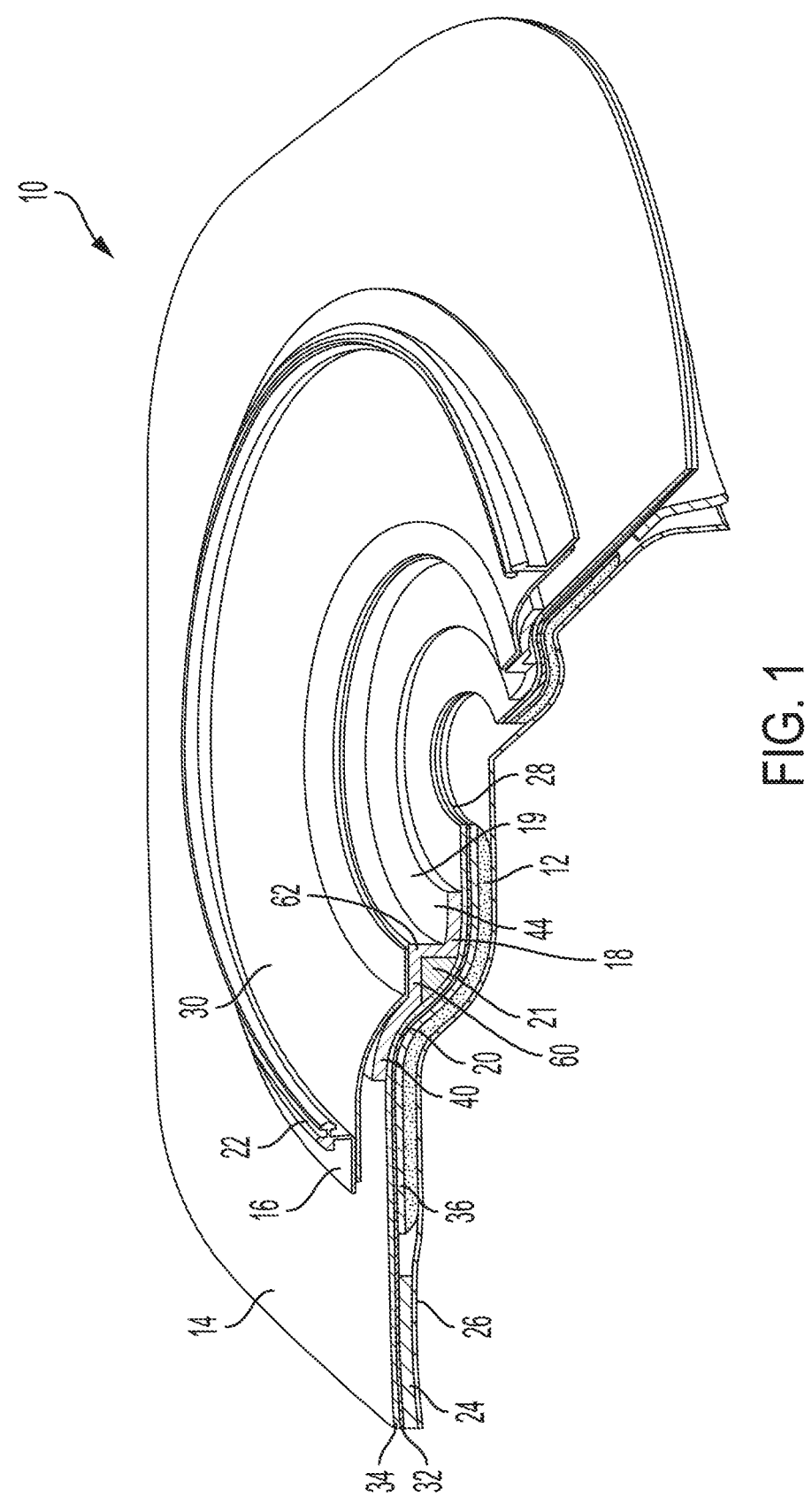
FIG. 1 is a perspective view of a convex ostomy barrier including a convex insert system according to an embodiment with a portion removed to illustrate its layered structure.
Figure 2:
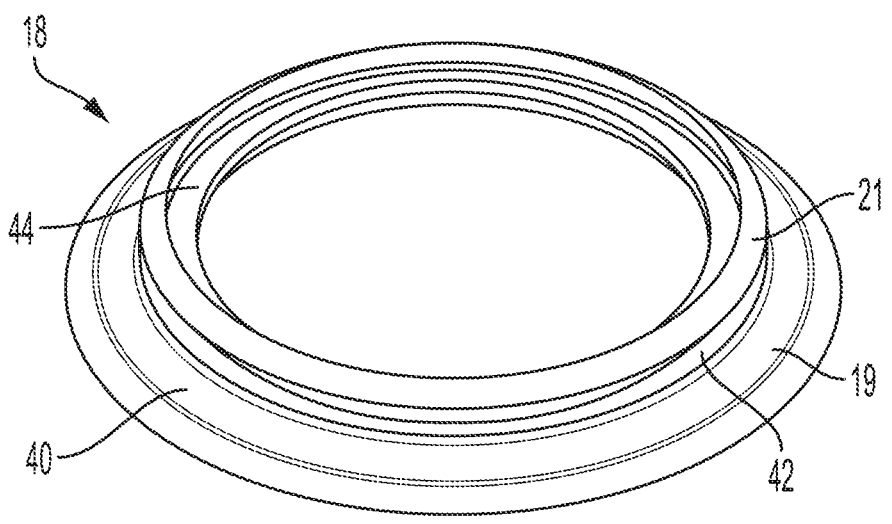
FIG. 2 is a perspective view of a convex insert system including a convex insert and a ring according to an embodiment.
Figure 3:
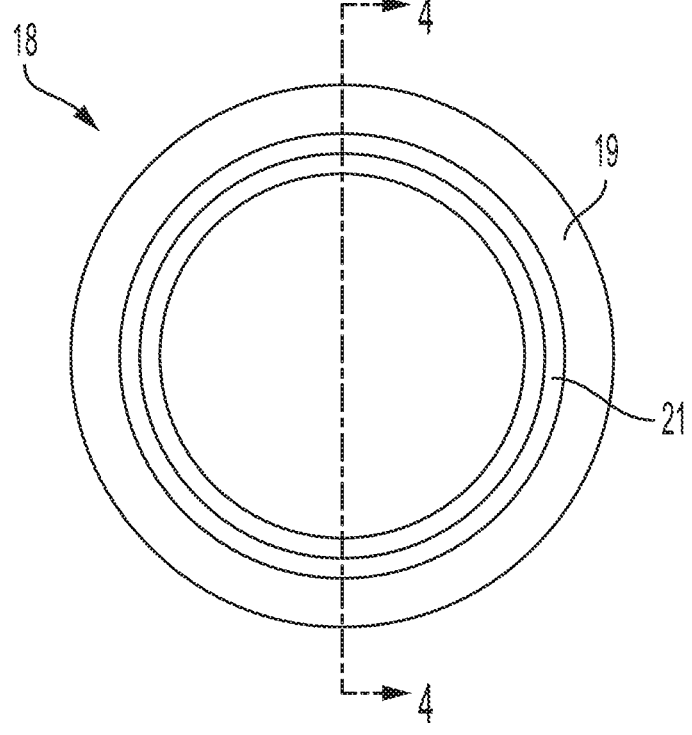
FIG. 3 is a schematic top view of the convex insert system of FIG. 2.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring to FIG. 1, a convex ostomy barrier 10 according to an embodiment is shown with a portion removed and viewed from a pouch-side to illustrate a layered construction of the convex ostomy barrier 10. The convex ostomy barrier 10 may be configured for a two-piece pouch system, and may generally comprise a skin barrier 12, a flange 16, a convex insert system 18, release liners 24, 26, and an inlet opening 28 for receiving a stoma.

FIGS. 2-5 are illustrations of the convex insert system 18 including a convex insert 19 and a ring 21 according to an embodiment. The convex insert 19 and the ring 21 may be configured to be assembled together to form the convex insert system 18 having a convex ring-like shaped body. The convex insert system 18 may be configured to provide the convexity of the convex ostomy barrier 10 to apply pressure around the peristomal area when the convex ostomy barrier 10 is attached to a user.

The softness/hardness of the convex ostomy system 18 may be determined by the combined softness/hardness of the convex insert 19 and the ring 21. As such, the softness/hardness of the convex ostomy system 18 may be easily altered or controlled by incorporating a ring 21 having a different softness/hardness. Such a feature may provide significant cost savings since convex ostomy barriers 10 of various convexity hardness/softness may be manufactured by making and incorporating rings 21 of various softness/hardness, instead of making convex inserts of various softness/hardness.

Figure 6:
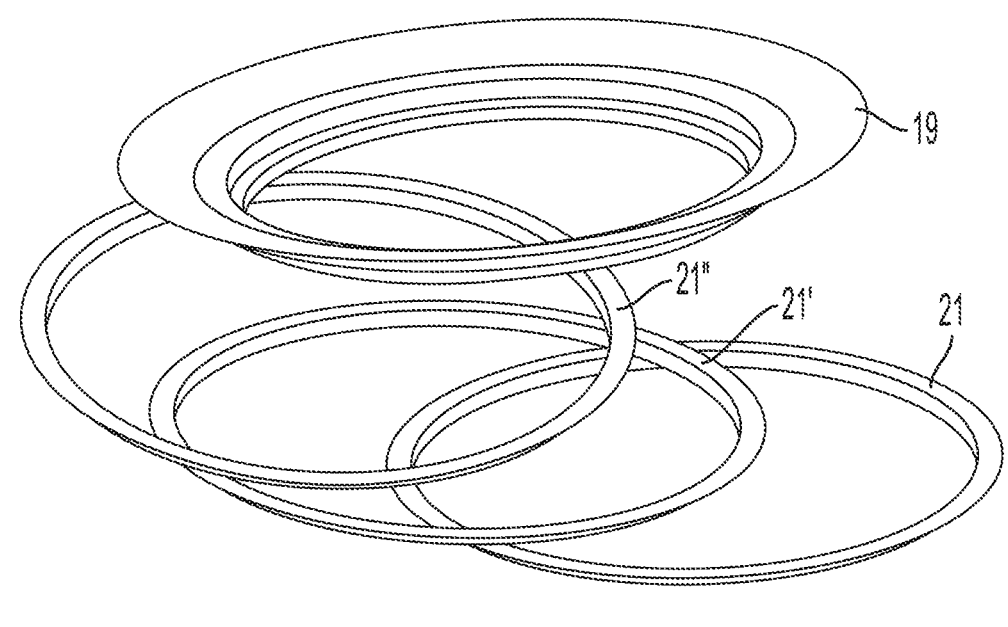
FIG. 6 is a perspective view of a convex insert and a plurality of rings according to an embodiment.

In FIG. 6, the convex insert 19 is illustrated with three rings 21, 21', 21". Each of the rings 21, 21', 21" may be configured to have a different softness/hardness. As such, a convex insert system prepared by assembling the convex insert 19 and the ring 21 may provide a first softness/hardness, and a convex insert system prepared by assembling the convex insert 19 and the ring 21' may provide a second softness/hardness that is different from the first softness/hardness, and a convex insert system prepared by assembling the convex insert 19 and the ring 21" may provide a third softness/hardness that is different from the first or second softness/hardness.

The convex insert 19 may be configured to protrude axially toward a body-side direction and configured to receive the ring 21 as shown in FIGS. 2-5. The convex insert 19 may include an outer flange 40, a middle portion 42, and an inner flange 44, and a radial wall 60 providing a generally flat pouch-side surface 64 on a pouch-side of the convex insert 19 for attachment of the flange 16. The outer flange 40 may include a concave body-side surface 50, which is configured to conform to a curved contour of a lower base portion 20 of a convex portion of the skin barrier 12. The radial wall 60 including the pouch-side surface 64 may be arranged in the middle portion 42. The middle portion 42 also may include a core-out portion 54 configured to receive the ring 21. The core-out portion 54 may be defined by the radial wall 60, which may radially extend from the outer flange 40 toward the inlet opening 28, and an axial wall 62, which may axially extend from the radial wall 60 toward a body-side direction. The inner flange 44 may radially extend from the axial wall 62 toward the inlet opening 28. The middle portion 42 may be configured to provide a step-like axial protrusion in the body-side direction from the outer flange 40 to the inner flange 44.

Figure 7:
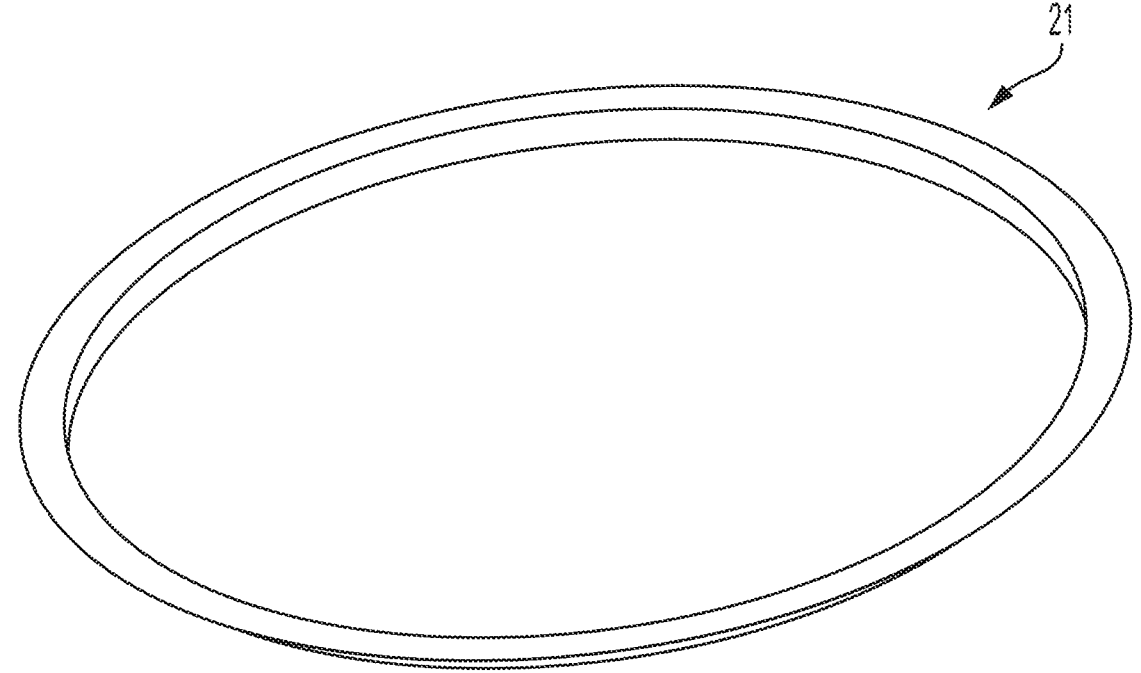
FIG. 7 is a perspective view of one of the rings of FIG. 6.

The ring 21 may have a relatively thin ring-like body as shown in FIGS. 6 and 7. The ring 21 may be configured such that the pouch-side of the ring 21 may fit in the core-out portion 54 of the convex insert 19 as best shown in FIGS. 4B60 and 5. In an embodiment, the ring 21 may include a radial pouch-side surface 70 and an axial pouch-side surface 72, and a sloped body-side surface 74. When received in the core-out portion 54 of the convex insert 19, the radial pouch-side surface 70 may be arranged adjacent the radial wall 60 of the convex insert 19 and the axial pouch-side surface 72 may be arranged adjacent the axial wall 72 of the convex insert 19. In such an embodiment, the body-side surface of the inner flange 44 of the convex insert 19, the sloped body-side surface 74 of the ring 21, and the body-side surface of the outer flange 49 of the convex insert 19 may form a generally continuous body-side surface of the convex insert system 18 as shown in FIG. 5.

The convex insert 19 and the ring 21 may be formed from the same or different materials. Suitable materials for the convex insert 19 and the ring 21 may include, but are not limited to, polymeric materials, rubber, silicone, and metallic materials. For example, the convex insert 19 and the ring 21 may be formed from a heat sealable thermoplastic material, such as ethylene vinyl acetate (EVA), thermoplastic elastomer, or thermoplastic urethane. In another example, the convex insert 19 and the ring 21 may be formed from a foam or silicone.

In FIG. 1, the convex insert system 18 is used in the convex ostomy barrier 10 for a two-piece pouch system, which may include the flange 16 having a body-side coupling ring 22 for attaching an ostomy pouch. In other embodiments, the convex insert system 18 including the convex insert 19 and the ring 21 may be used in a convex ostomy barrier for a one-piece pouch system. The body-side coupling ring 22 may be configured to mate with a pouch-side coupling ring (not shown), such that the ostomy pouch may be mechanically secured to the ostomy barrier 10 when the coupling rings are engaged with each other. The flange 16 may be attached to the convex insert 19 via a flange film 30. In the embodiment of FIG. 1, the flange 16 is attached to a pouch-side surface of the flange film 30 proximate an outer periphery of the flange film 30. The convex insert 19 may be attached to a body-side surface of the flange film 30 proximate an inner peripheral portion of the flange film 30, such that the flange 16 and the convex insert 19 are attached on the opposite surfaces of the flange film 30 at opposite ends. Such a configuration provides a floating flange feature, in which a user may insert his/her finger between the flange 16 and the convex insert 19 to facilitate engagement of the coupling rings to attach a pouch to the ostomy barrier 10.

The skin barrier 12 may be arranged on the body-side surface of the ostomy barrier 10 for attachment to a user. The inlet opening 28 may be defined by an inner periphery of the skin barrier 12 for receiving a stoma (not shown.) The skin barrier 12 may be formed from a suitable medical-grade adhesive that can adhesively secure the ostomy barrier 10 to a patient's skin in the peristomal region, such as a hydrocolloid adhesive composition.

The ostomy barrier 10 may also include a tape 14 including an adhesive layer 32 and a backing layer 34. In some embodiments, the skin barrier 12 may include a backing layer 36 laminated on the pouch-side surface of the skin barrier 12. The backing layer 36 may be formed from a suitable heat sealable polymeric material, such that the backing layer 36 may be heat sealed to the tape 14.

In the embodiment of FIG. 1, the skin barrier 12 is attached to a portion of the adhesive layer 32 proximate the inlet opening 28 with the backing layer 36 therebetween. In such an embodiment, an outer peripheral portion of the adhesive layer 32 may be attached to a user surrounding the skin barrier 12 to provide additional security.

The adhesive layer 32 of the tape 14 may be formed from a suitable medical adhesive, such as an acrylic adhesive. The backing layer 34 may be formed from a suitable material, such as a nonwoven material or a thin polymeric film.

In other embodiments, the ostomy barrier 10 may not include the tape 14. In such an embodiment, the skin barrier 12 may be the only means for attaching the ostomy barrier 10 to a user.

In the embodiment of FIG. 1, the convex insert system 18 may be attached to the backing layer 34 of the tape 14 to provide a convexity to the skin barrier 12. In other embodiments, the convex insert system 18 may be attached to a pouch-side surface of the skin barrier 12.

In the embodiment of FIG. 1, the flange film 30 may be attached to the pouch-side surface 64 of the convex insert 19 to secure the flange 16. For example, the flange film 30 may be heat sealed to the pouch-side surface 64 of the convex insert 19. As shown in FIG. 1, the body-side surfaces of the outer flange 40 of the convex insert 19, the sloped body-side surface 74 of the ring 21, and the body-side surface of the inner flange 44 of the convex insert 19 may be in contact with the tape 14, wherein at least some portions of which are attached to the backing layer 34. For example, the body-side surface of the outer flange 40 may be heat sealed to the backing layer 34 of the tape 14. In another example, an adhesive may be provided on the body-side surface of the convex insert system 18 for attachment to the tape 14.

A release liner may be provided to cover the skin barrier 12 and the tape 14. In the embodiment of FIG. 1, the release liner 24 is provided to cover an outer peripheral portion of the tape 14, and the release liner 26 is provided to cover the entire body-side surface of the ostomy barrier 10 including the skin barrier 12 and the tape 14. In use, the release liner 26 may be removed first for attachment of the skin barrier 12 to peristomal skin, and the release liner 24 may be removed subsequently to expose the tape 14 for further attachment to user's skin.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A convex ostomy barrier for attaching an ostomy appliance to a peristomal skin surrounding a stoma, the convex ostomy barrier comprising: a skin barrier formed from a skin friendly adhesive; an inlet opening for receiving a stoma; and a convex insert system arranged adjacent the skin barrier and configured to provide a convex body-side contour of the convex ostomy barrier, wherein the convex insert system includes a convex insert and a ring, wherein the convex insert and the ring are configured to be assembled together to form the convex insert system in which a sloped body-side surface of the ring is in abutment with and intermediate a body-side surface of an inner flange of the convex insert and a body-side surface of an outer flange of the convex insert to form a continuous body-side surface of the convex insert system, wherein continuous body-side surface of the convex insert system comprises the body-side surface of the ring, the body-side surface of the inner flange, and the body-side surface of the outer flange; wherein the ring is selected from a plurality of rings in accordance with a characteristic thereof, and wherein the plurality of rings comprises a first ring having a first characteristic and a second ring having a second characteristic and the ring is a selected one of the first ring and the second ring, wherein the convex ostomy barrier including the convex insert system formed from the convex insert and the first ring has a first barrier characteristic, and the convex ostomy barrier including the convex insert system formed from the convex insert and the second ring has a second barrier characteristic, wherein the first barrier characteristic is different than the second barrier characteristic.

2. The convex ostomy barrier of claim 1, wherein the convex insert includes a core-out portion configured to receive the ring, wherein the ring is arranged in the core-out portion of the convex insert to form the convex insert system having a convex ring-like body.

3. The convex ostomy barrier of claim 2, wherein the convex insert comprises a middle portion including the core-out portion, wherein the inner flange and the outer flange are connected by the middle portion and arranged in different axial planes, wherein the convex insert system is configured to support the skin barrier on a body-side surface.

4. The convex ostomy barrier of claim 3, wherein the convex insert includes a radial wall radially extending from the outer flange toward the inlet opening, and an axial wall extending axially from the radial wall in a body-side direction, wherein the core-out portion is defined by the radial wall and the axial wall on a body-side, wherein the inner flange extends from the axial wall toward the inlet opening, and wherein the outer flange, the middle portion, and the inner flange provides a step-like protrusion in the body-side direction.

5. The convex ostomy barrier of claim 1, further comprising a flange including a coupling ring, wherein the flange is attached to a pouch-side surface of the radial wall of the convex insert.

6. The convex ostomy barrier of claim 1, wherein the convex ostomy barrier is configured to have a first softness/hardness comprising the convex insert system formed from the convex insert and the ring having a first characteristic, wherein the convex ostomy barrier is configured to have a second softness/hardness comprising the convex insert system formed from the convex insert and the ring having a second characteristic; wherein the first softness/hardness is different from the second softness/hardness and the first characteristic is different from the second characteristic.

* * * * *